United States Patent
Levi et al.

(10) Patent No.: US 6,602,183 B1
(45) Date of Patent: Aug. 5, 2003

(54) ENHANCED SUCTION-BASED CARDIAC MECHANICAL STABILIZER

(75) Inventors: Tamir Levi, Haifa; Benny Rousso, Bat-Yam, both of (IL)

(73) Assignee: Inpulse Dynamics NV, Curacao (AN)

( * ) Notice: Subject to any disclaimer, the term of this patent is extended or adjusted under 35 U.S.C. 154(b) by 0 days.

(21) Appl. No.: 09/624,089

(22) Filed: Jul. 24, 2000

(51) Int. Cl.[7] .............................. A61F 2/00; A61F 13/00

(52) U.S. Cl. ........................................................ 600/37

(58) Field of Search .................... 600/37, 201; 128/897, 128/898; 606/1, 205

(56) References Cited

U.S. PATENT DOCUMENTS

| | | | | |
|---|---|---|---|---|
| 3,587,567 A | * | 6/1971 | Schiff ........................... | 600/37 |
| 5,906,607 A | * | 5/1999 | Taylor et al. .................... | 606/1 |
| 5,927,284 A | * | 7/1999 | Borst et al. .................... | 600/37 |
| 6,032,672 A | * | 3/2000 | Taylor ........................... | 600/37 |
| 6,251,065 B1 | * | 6/2001 | Kochamba et al. ............. | 600/37 |

FOREIGN PATENT DOCUMENTS

| | | |
|---|---|---|
| WO | WO 97/25098 | 7/1997 |
| WO | WO 00/72918 | 12/2000 |

OTHER PUBLICATIONS

Borst, et al., "Coronary artery bypass grafting without cardiopulmonary bypass and without interuption of native coronary flow using a novel anastomosis site restraining device ('Octopus')", Journal of the American College of Cardiology, 27(6), May 1996.

U.S. Patent Application No.: 09/320,090, entitled "Local Cardiac Motion Control Using Applied Electrical Signals", filed: May 26, 1999.

Burfeind, et al., "The effects of mechanical stabillization on left ventricular performance", European Journal of Cardio-Thoracic Surgery, 14(1998), pp. 285–289.

* cited by examiner

*Primary Examiner*—Max F. Hindenburg
*Assistant Examiner*—Brian Szmal
(74) *Attorney, Agent, or Firm*—Reed Smith LLP; William H. Dippert (57) ABSTRACT

Apparatus is provided for performing a medical procedure on a beating heart. A stabilization element is applied to a segment of the heart in order to reduce motion of the segment. A plurality of suction ports are positioned on the stabilization element so as to form respective seals with the segment of the heart while the stabilization element is applied to the segment. The suction ports apply suction forces to the segment of the heart so as to maintain the segment in contact with the stabilization element. A suction control assembly is coupled to the ports. At least one of the suction ports maintains its seal with the segment of the heart even when another one of the suction ports does not form a seal with the segment of the heart.

26 Claims, 6 Drawing Sheets

ENHANCED SUCTION-BASED CARDIAC MECHANICAL STABILIZER

FIELD OF THE INVENTION

The present invention relates generally to invasive devices and methods for treatment of the heart, and specifically to devices and methods for controlling the heart muscle during surgery.

BACKGROUND OF THE INVENTION

Heart surgery is often accompanied by the induction of cardioplegia (elective stopping of essentially all cardiac activity by injection of chemicals, selective hypothermia, mechanical stabilization, or electrical stimuli). In humans, induced global cardioplegia is nearly always practiced in conjunction with cardiopulmonary bypass.

Recently, minimally-invasive methods of cardiac surgery have been developed, in which the heart is approached through an incision made between the ribs, without sternotomy. It is sometimes preferred that, rather than inducing cardioplegia, the surgeon mechanically restrains a portion of the heart on which a surgical procedure, such as a bypass graft, is to be performed. Various tools and methods have been developed for this purpose, such as: (a) a suction cup-based stabilization platform (e.g., the Utrecht Octopus); (b) mechanical stabilization devices, such as the Ultima OPCAB System, produced by Guidant, Inc. (Indianapolis, Ind.); (c) the Octopus 2 or the EndoOctopus device, both produced by Medtronic, Inc. (Minneapolis, Minn.); (d) a U-shaped metal foot and other stabilizers produced by Genzyme Surgical Products, Inc. (Tucker, Ga.); (e) the Octopus Suction stabilizer, produced by Medtronic GmbH, Germany; and (f) CardioVations mechanical stabilizers produced by Ethicon Endo-Surgery (Cincinnati, Ohio).

An article entitled "Coronary artery bypass grafting without cardiopulmonary bypass and without interruption of native coronary flow using a novel anastomosis site restraining device ('Octopus')," by Borst et al., Journal of the American College of Cardiology, 27(6) (May 1996), pp. 1356–1364, which is incorporated herein by reference, describes use of the Octopus suction-generating device during experimental surgery on in situ pig hearts.

Such mechanical restraint of the heart muscle requires that substantial force, e.g., pressure or vacuum, be applied, which can cause tissue trauma. The effects of mechanical stabilization are described in an article, "The effects of mechanical stabilization on left ventricular performance," by Burfeind et al., European Journal of Cardio-Thoracic Surgery, 14(1998), pp. 285–289, which is incorporated herein by reference.

SUMMARY OF THE INVENTION

It is an object of some aspects of the present invention to provide improved methods and apparatus for regulating motion of the heart.

It is a further object of some aspects of the present invention to provide improved methods and apparatus for reducing motion of the heart during minimally-invasive and open-chest surgery.

It is yet a further object of some aspects of the present invention to provide improved methods and apparatus for applying mechanical force to reduce motion of the heart during minimally-invasive and open-chest surgery.

It is still a further object of some aspects of the present invention to provide improved methods and apparatus for reducing motion of the heart during minimally-invasive and open-chest surgery, while minimizing or substantially eliminating injury to the heart resulting from the motion reduction.

In preferred embodiments of the present invention, cardiac control apparatus inhibits motion of a segment of a patient's heart, while allowing the heart to continue to pump blood. The reduction in motion of the segment, as provided by these embodiments of the present invention, is typically used to enable a surgeon to perform minimally-invasive surgery or open-chest surgery, generally without inducing global cardioplegia or requiring cardiopulmonary bypass. The cardiac control apparatus comprises a stabilization element, which has a surface that is applied to the heart in order to reduce motion thereof. Additionally, a plurality of suction ports are positioned on the surface of the stabilization element. When the element is applied to the segment of the heart, the ports apply suction to the segment of the heart, so as to maintain contact between the heart and the stabilization element, and to thereby reduce motion of the segment. Preferably, the ports are configured such that if one of the suction ports loses contact with the surface of the heart, at least one of the other ports will continue to apply suction to the heart. In this manner, the loss of contact substantially does not inhibit the overall functioning of the cardiac control apparatus.

By contrast to these embodiments of the present invention, prior art mechanical stabilizers (such as the Medtronic Octopus) fix a plurality of suction ports to the stabilization element in a configuration that assures that if even one of the suction ports loses contact with the heart, then all of the suction ports will fail to operate. In order to avoid this eventuality, prior art mechanical stabilizers must apply a high level of suction through each of the ports (e.g., 400 millibars), so as to guarantee that throughout the medical procedure, all of the suction ports maintain their contact with the heart. The inventors believe that the application of such a strong suction to the epicardium risks injuring the affected tissue. This structural drawback of prior art stabilizers derives from their use of a single suction line that is directly coupled to all of the ports. Thus, if one of the ports even temporarily loses contact with the heart, then it effectively causes a short-circuit, whereby that port becomes the path of least resistance for air to flow into the suction line, and the desired negative air pressure at the other suction ports disappears.

Therefore, an advantage of these embodiments of the present invention is that significantly lower levels of suction can be applied through every port, because at least some of the suction ports will continue to function even if some others of the suction ports have lost contact with the surface of the heart. It is believed that these lower levels of suction (typically under 200 millibars) will substantially reduce or eliminate injury to the heart responsive to the application of suction thereto.

In a preferred embodiment of the present invention, each of the suction ports is coupled by a respective suction line to a vacuum source, typically external to the stabilization element. In this configuration, each suction port acts substantially independently of each of the other ports, and is therefore unaffected by whether the other ports are in contact with the heart.

Alternatively, at least one of the suction lines has a plurality of suction ports coupled thereto. This configuration allows greater simplicity of the stabilization element, by reducing the number of suction lines used to hold the surface of the heart in contact with the stabilization element. Preferably, a sufficient number of suction lines are utilized such that even if one of the ports on a multi-port suction line fails—thereby generally disabling the other ports on the same line—one or more other ports not coupled to the same line will still continue to function. Optionally, some or all of the ports coupled to the multi-port suction line are coupled thereto through respective valves, which are adapted to close when the suction port loses its seal with the surface of the heart. In this manner, even when a plurality of ports are coupled to the same line, the failure of one of the ports does not adversely affect the functioning of the other ports.

For some applications of the present invention, a plurality of ports on the surface of the stabilization element are coupled through respective small orifices to a relatively-large chamber, typically within the stabilization element. The chamber is coupled, in turn, to the vacuum source. Preferably, the volume of the chamber is sufficiently large and the cross-sectional areas of the orifices are sufficiently small, such that if one of the suction ports loses its seal with the heart, and air enters the chamber through the orifice coupled to the port, then the negative pressure within the chamber will not be significantly affected. Since the overall negative pressure within the chamber substantially does not change when one of the ports coupled thereto loses its seal with the heart, the other ports coupled to the chamber will continue to function.

In a preferred embodiment, a control unit of the cardiac control apparatus or a human operator of the apparatus reduces the level of suction applied by some or all of the ports, until at least one of the ports loses its seal with the surface of the heart. At this point, most or all of the other ports preferably continue to apply suction, because the stabilization element is preferably configured such that some of the ports can continue to apply suction even when some others of the ports lose effective contact with the heart. It is noted that this embodiment of the present invention allows the cardiac control apparatus to operate at suction levels significantly lower than are possible using the prior art apparatus described hereinabove, because the prior art apparatus must apply high levels of suction so as to guarantee that all of the suction ports are operative.

In a preferred embodiment, the level of suction applied by one or more of the ports is intermittently or continuously varied, responsive to measurements indicative of the number of suction ports which are effectively securing the heart. Optionally, the suction level is also set based on measurements indicative of a physiological parameter, such as heart rate, left ventricular pressure (LVP), or motion of the heart. For example, suction may be decreased responsive to a decrease in the patient's heart rate, because reduced heart rate is typically associated with a lower probability that the suction ports will lose effective contact.

In a preferred embodiment, the level of applied suction is modulated in coordination with other means for stabilizing the segment of the heart, e.g., cardioplegia-inducing drugs, mechanical force applied by the stabilization element, or electrical signals applied to the heart. For example, if the application of cardioplegia-inducing drugs is being decreased, the level of suction may be increased.

Optionally, electrical signals are applied through electrodes fixed to the stabilization element or placed directly on the surface of the heart. Preferred methods and apparatus for applying signals to the heart, as well as for detecting electrical activity generated by the heart, are described in a PCT patent application entitled, "Local cardiac motion control using applied electrical signals and mechanical force," filed May 25, 2000, and in U.S. patent application Ser. No. 09/320,090, entitled "Local cardiac motion control using applied electrical signals." Both of these applications are assigned to the assignee of the present patent application and are incorporated herein by reference. In addition, signals described in PCT Patent Publication WO 97/25098, and in the corresponding U.S. National Phase patent application Ser. No. 09/101,723, entitled, "Electrical muscle controller," may be applied to the heart through electrodes coupled to the stabilization element or through electrodes applied directly to the heart. Typically, the level of suction is increased or decreased in coordination with the signals applied to the heart, so as to reduce motion of the segment while generally assuring that systemic oxygen demands are met.

There is therefore provided, in accordance with a preferred embodiment of the present invention, apparatus for performing a medical procedure on a beating heart, including:

a stabilization element, adapted to be applied to a segment of the heart in order to reduce motion of the segment;

a plurality of suction ports, positioned on the stabilization element so as to form respective seals with the segment of the heart while the stabilization element is applied to the segment, which suction ports are adapted to apply suction forces to the segment of the heart so as to maintain the segment in contact with the stabilization element; and a suction control assembly, coupled to the ports, such that at least one of the suction ports is adapted to maintain its seal with the segment of the heart even when another one of the suction ports does not form a seal with the segment of the heart.

Preferably, the suction control assembly includes:

a first suction line, adapted to convey negative air pressure to a first one of the suction ports; and a second suction line, adapted to convey negative air pressure to a second one of the suction ports, wherein a level of negative air pressure in the first suction line is substantially independent of a level of negative air pressure in the second suction line, when the stabilization element is applied to the segment of the heart.

Alternatively or additionally, the suction control assembly includes:

a first suction line, which is adapted to convey negative air pressure to two or more of the suction ports; and a second suction line, which is adapted to convey negative air pressure to one or more of the suction ports, wherein a level of negative air pressure in the second suction line is substantially independent of a level of negative air pressure in the first suction line, when the stabilization element is applied to the segment of the heart.

Further alternatively or additionally, the suction control assembly includes a valve coupled to one of the suction ports, which valve is adapted to close when the suction port coupled thereto does not form a seal with the segment of the heart.

In a preferred embodiment, the stabilization element is adapted to be applied to the segment of the heart so as to enable a therapeutic medical procedure to be performed on the heart. Alternatively or additionally, the stabilization element is adapted to be applied to the segment of the heart so as to enable a diagnostic medical procedure to be performed on the heart.

In a preferred embodiment, the suction control assembly includes a chamber having negative air pressure therein when the stabilization element is applied to the segment of the heart. The chamber is coupled through respective orifices to the suction ports. A characteristic of the orifices is such that, when one of the suction ports does not form a seal with the segment of the heart, a magnitude of the negative air pressure within the chamber is maintained to such an extent that one or more of the other suction ports maintain their seals with the segment of the heart. Preferably, the characteristic of the orifices includes cross-sectional areas of the orifices.

Alternatively or additionally, the apparatus includes:
- a vacuum source, adapted to generate negative air pressure; and
- a control unit, adapted to couple the negative air pressure to the plurality of suction ports, so as to apply to the segment of the heart the suction forces which maintain the segment in contact with the stabilization element.

In a preferred embodiment, the control unit is adapted to couple the negative air pressure to the suction ports, such that a first one of the suction ports applies to the segment of the heart a first level of negative air pressure, and a second one of the suction ports applies to the segment of the heart a second level of negative air pressure.

In a preferred embodiment, the apparatus includes a force sensor, adapted to convey to the control unit a force signal responsive to a force applied by the stabilization element to the segment of the heart, wherein the control unit is adapted to modulate a magnitude of the negative air pressure applied to one or more of the suction ports responsive to the force signal.

Alternatively or additionally, the apparatus includes a sensor, adapted to convey to the control unit a sensor signal indicative of a number of the suction ports not forming a seal with the segment of the heart, wherein the control unit is adapted to modulate a magnitude of the negative air pressure applied to two or more of the ports, so as to generally maintain a determined number of the suction ports not forming respective seals with the segment of the heart. In a preferred embodiment, the control unit is adapted to modulate the magnitude of the negative air pressure applied to two or more of the ports, so as to generally maintain exactly one of the suction ports not forming a seal with the segment of the heart.

Optionally, the apparatus includes an electrode, adapted to be placed on the heart and to convey a signal to the control unit responsive to electrical activity of the heart, wherein the control unit is adapted to modulate a magnitude of the negative air pressure applied to one or more of the suction ports responsive to the signal. Further optionally, the electrode is fixed to the stabilization element.

In a preferred embodiment, the apparatus includes a motion sensor, adapted to convey to the control unit a motion signal responsive to motion of the heart, wherein the control unit is adapted to modulate a magnitude of the negative air pressure applied to one or more of the suction ports responsive to the motion signal. Optionally, the motion sensor is fixed to the stabilization element. Further optionally, the control unit is adapted to reduce the magnitude of the negative air pressure responsive to a motion signal indicative of reduced motion of the heart. Alternatively or additionally, the control unit is adapted to increase the magnitude of the negative air pressure responsive to a motion signal indicative of increased motion of the heart.

In a preferred embodiment, the apparatus includes a sensor, coupled to the control unit and to the suction ports, wherein the control unit is adapted to reduce a magnitude of the negative air pressure applied to two or more of the ports, and to terminate reducing the magnitude of the negative air pressure when the sensor conveys a sensor signal indicative of one or more of the suction ports not forming respective seals with the segment of the heart. Typically, the sensor includes an air-pressure sensor or an air-flow sensor.

In a preferred embodiment, the apparatus includes an electrode, adapted to be placed on the heart, wherein the control unit is adapted to drive the electrode to apply a signal to the heart which modulates mechanical behavior of the heart. Preferably, the electrode is fixed to the stabilization element. Further preferably, the control unit is adapted to drive the electrode to apply the signal to the heart so as to reduce motion of the heart. Optionally, the control unit is adapted to regulate a magnitude of the negative air pressure applied to the segment of the heart by at least one of the suction ports in conjunction with driving the electrode to apply the signal.

In a preferred embodiment, the plurality of suction ports include:
- a test port; and
- a set of other ports,
- wherein, for a given level of negative air pressure applied to the test port and to the set of other ports, the other ports are adapted to have a higher probability than the test port of remaining sealed to the segment of the heart.

Preferably, the test port includes a pressure regulator including an input and an output thereof, the pressure regulator being adapted to be coupled at the input to air at a first magnitude of air pressure, and to be coupled to apply, at the output, air at a second magnitude of air pressure which is lower than the first magnitude.

There is further provided, in accordance with a preferred embodiment of the present invention, a method for performing a medical procedure on a beating heart, including:
applying a stabilization element to a segment of the heart, so as to reduce motion of the segment; and
applying suction forces to the segment of the heart through a plurality of suction ports that are positioned on the stabilization element, so as to form respective seals with the segment of the heart while the stabilization element is applied to the segment, and so as to maintain the segment in contact with the stabilization element,
such that at least one of the suction ports maintains its seal with the segment of the heart even when another one of the suction ports does not form a seal with the segment of the heart.

In a preferred embodiment, applying the suction forces includes conveying negative air pressure to first and second ones of the suction ports, such that a level of the negative air pressure conveyed to the first suction port is substantially independent of a level of the negative air pressure applied to the second suction port, when the stabilization element is applied to the segment of the heart.

Alternatively or additionally, applying the suction forces to the segment of the heart includes:
conveying negative air pressure to two or more of the suction ports through a first suction line; and
conveying negative air pressure to one or more of the suction ports through a second suction line,
wherein a level of negative air pressure in the second suction line is substantially independent of a level of negative air pressure in the first suction line, when the stabilization element is applied to the segment of the heart.

In a preferred embodiment, applying the suction forces includes conveying negative air pressure from a chamber through respective orifices to the suction ports, such that, when one of the suction ports does not form a seal with the segment of the heart, a magnitude of the negative air pressure within the chamber is maintained to such an extent that one or more of the suction ports maintain their seals with the segment of the heart.

Alternatively or additionally, applying the suction forces includes closing a valve coupled to one of the suction ports when the suction port coupled to the valve does not form a seal with the segment of the heart.

In a preferred embodiment, applying the suction forces includes regulating negative air pressure applied to the suction ports such that a first one of the suction ports applies to the segment of the heart a first magnitude of negative air pressure, and a second one of the suction ports applies to the segment of the heart a second magnitude of negative air pressure.

Preferably, regulating includes:

regulating the second magnitude of negative air pressure to be lower than the first magnitude, while generally simultaneously reducing the first and second magnitudes of negative air pressure; and discontinuing reducing the magnitudes of negative air pressure when the first port forms a seal and the second port does not form a seal.

In a preferred embodiment, the method includes receiving a force signal responsive to a force applied by the stabilization element to the segment of the heart, wherein applying the suction forces includes modulating a magnitude of negative air pressure applied to one or more of the suction ports responsive to the force signal.

Alternatively or additionally, the method includes receiving a signal responsive to electrical activity of the heart, wherein applying the suction forces includes modulating a magnitude of the negative air pressure applied to one or more of the suction ports responsive to the signal.

Further alternatively or additionally, the method includes receiving a motion signal responsive to motion of the heart, wherein applying the suction forces includes modulating a magnitude of the negative air pressure applied to one or more of the suction ports responsive to the motion signal. Preferably, modulating the magnitude of the negative air pressure includes reducing the magnitude of the negative air pressure responsive to a motion signal indicative of reduced motion of the heart. Alternatively or additionally, modulating the magnitude of the negative air pressure includes increasing the magnitude of the negative air pressure responsive to a motion signal indicative of increased motion of the heart.

In a preferred embodiment, applying the suction forces includes:

reducing a magnitude of the negative air pressure applied to two or more of the ports;

receiving a signal which is indicative of one or more of the suction ports losing their respective seals with the segment of the heart responsive to the reduced magnitude of the negative air pressure; and terminating reducing the magnitude of the negative air pressure responsive to receiving the signal.

In a preferred embodiment, the method includes driving an electrode to apply a signal to the heart which further reduces motion of the heart. Preferably, applying the suction forces includes regulating a magnitude of the suction forces applied by one or more of the suction ports to the segment of the heart in conjunction with driving the electrode to apply the signal.

In a preferred embodiment, the method includes receiving a sensor signal indicative of a number of the suction ports not forming a seal with the segment of the heart, wherein applying the suction forces includes modulating a magnitude of the negative air pressure applied to two or more of the ports, so as to generally maintain a determined number of the suction ports not forming respective seals with the segment of the heart. Preferably, modulating the magnitude of the negative air pressure includes modulating the pressure so as to generally maintain exactly one of the suction ports not forming a seal with the segment of the heart.

The present invention will be more fully understood from the following detailed description of the preferred embodiments thereof, taken together with the drawings, in which:

DETAILED DESCRIPTION OF PREFERRED EMBODIMENTS

Figure 1:
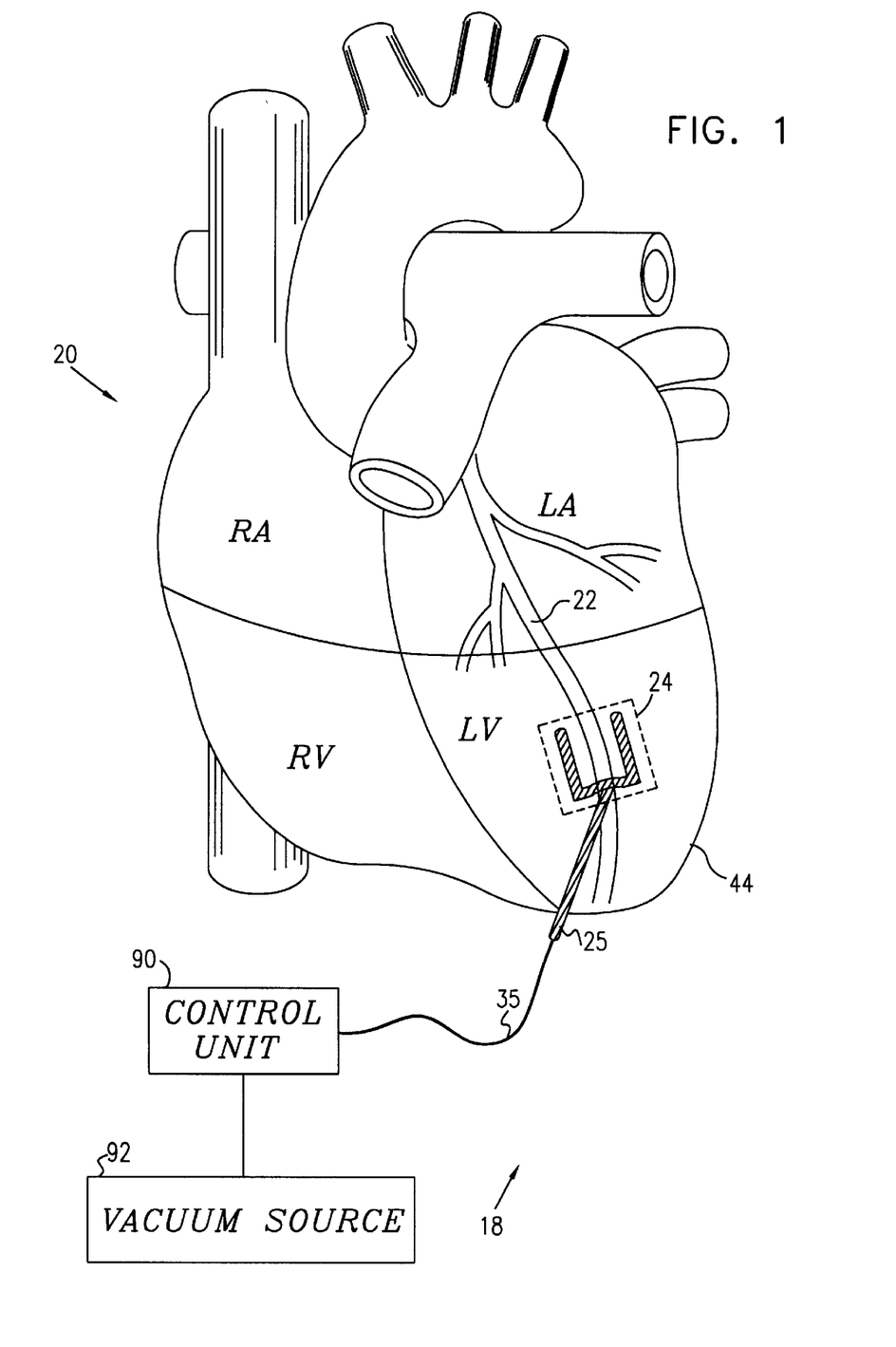
FIG. 1 is a schematic illustration of the external surface of a heart, showing the placement of a stabilization element thereon, in accordance with a preferred embodiment of the present invention.
Figure 2:
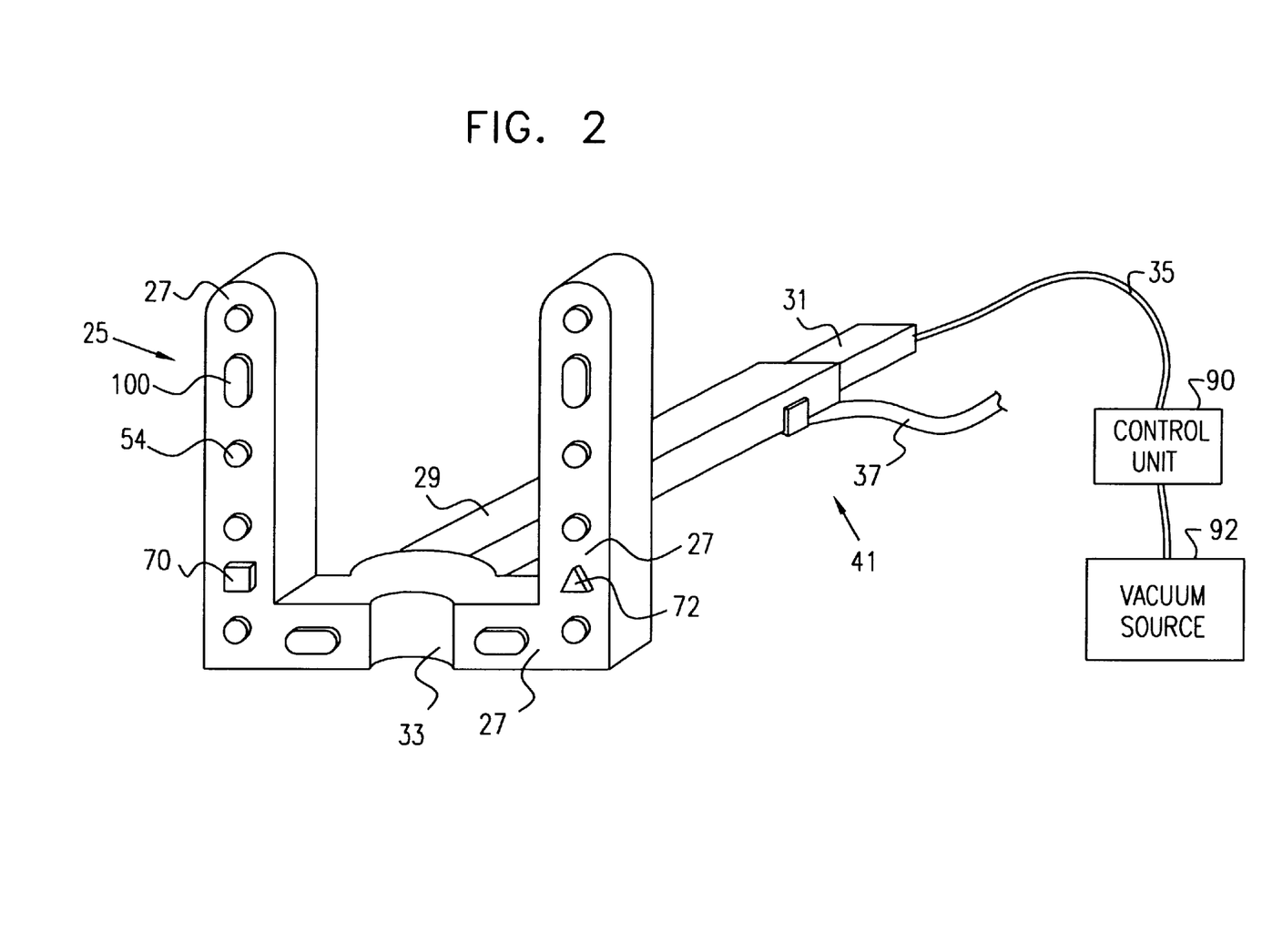
FIGS. 2–7 are schematic illustrations of the stabilization element, in accordance with respective preferred embodiments of the present invention.

Reference is made to FIGS. 1 and 2. FIG. 1 is a schematic illustration of apparatus 18, comprising a stabilization element 25 for reducing the motion of a segment 24 of a patient's heart 20 during surgery, in accordance with a preferred embodiment of the present invention. FIG. 2 is a schematic illustration of stabilization element 25, in accordance with a preferred embodiment of the present invention. A surface 27 of stabilization element 25 is placed on segment 24, so as to apply a mechanical force thereto. Preferably, a plurality of suction ports 54 on surface 27 are coupled through a control unit 90 of apparatus 18 to a vacuum source 92. At least some of the suction ports hold the surface of the heart in contact with the stabilization element, thereby reducing motion of segment 24. As described hereinbelow with reference to FIGS. 3–8, the ports are preferably configured such that if one of the ports breaks its suction seal with the heart, then at least one of the other ports will continue to apply suction thereto, so as to maintain the stabilization element in contact with the heart. For some applications, the force applied to the heart additionally includes a positive pressure exerted by surface 27 of the element on heart 20. Typically, but not necessarily, surface 27 is roughened, coated with silicone, or otherwise configured so as to reduce or eliminate any slip between surface 27 and segment 24.

Optionally, one or more electrodes 100 coupled to surface 27 are actuated by control unit 90 to apply electrical signals to heart 20 and/or to sense electrical activity of the heart. The electrical signals typically reduce motion of the heart, but may, alternatively or additionally, pace the heart or intermittently enhance or otherwise modulate motion of the heart. Preferred methods and apparatus for utilizing electrodes 100 are described in the above-referenced PCT patent application, entitled, "Local cardiac motion control using applied electrical signals and mechanical force."

Optionally, a handle 41 of stabilization element 25 has two members 29 and 31, which are slidably coupled to each other. Lines 35 preferably pass through handle 41, to couple control unit 90 to suction ports 54, optional electrodes 100, and sensors 70 and 72, described hereinbelow. For some applications, lines 35 couple additional electrodes, sensors, and actuated devices (not shown) on the stabilization element to control unit 90. To simplify the performance of open-chest procedures, a connecting member 37 typically couples handle 41 to a chest retractor (not shown), so as to keep the stabilization element generally stationary with respect to the patient's chest.

An elevated portion 33 of stabilization element 25 preferably enables surface 27 of the element to be placed on segment 24, without directly compressing a particular site within the segment. Thus, for example, elevated portion 33 may be placed over the left anterior descending artery 22 of heart 20, so as not to restrict blood flow through the artery. Optionally, one or more liquid/gas transport elements (not shown) on elevated portion 33 or elsewhere on the stabilization element apply one or more materials, such as physiological saline solution, gaseous CO2, and/or air to the surface of heart 20, so as to keep the surgery site moist and/or clear of blood. Alternatively or additionally, these elements perform functions similar to those described with respect to transport elements in the above-referenced PCT patent application, which was filed May 25, 2000.

Optionally, a plurality of motion sensors 70 (e.g., accelerometers) and one or more supplemental sensors 72 are coupled to stabilization element 25, to the heart, or to another site on or in the patient's body. Sensors 72 may comprise, for example, a systemic blood pressure sensor, an LVP sensor, a pO2 sensor, a pCO2 sensor, a flow rate sensor, and/or a force sensor, which measures a contact force between stabilization element 25 and heart 20. The electrodes and sensors (optionally in combination with other electrodes and sensors not coupled to the stabilization element) provide substantially continuous monitoring of the patient's vital signs, in order to ensure that all of the signs are maintained within a safe range during the surgery. To the extent that any of the vital signs is outside the range, control unit 90 will either take corrective action on its own and/or provide an alarm to the surgeon, who will then be able to respond appropriately. Alternatively or additionally, control unit 90 varies aspects of the application of suction through one or more of ports 54 responsive to signals generated by the various electrodes and sensors. A preferred method is described hereinbelow with reference to FIG. 8.

Figure 3:
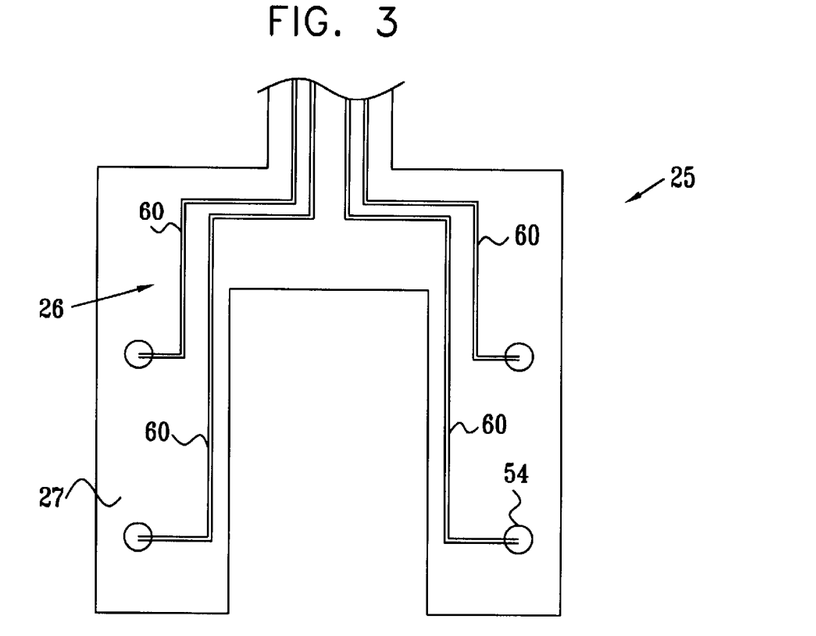

FIG. 3 is a schematic illustration of stabilization element 25, in accordance with a preferred embodiment of the present invention. In this embodiment, a suction control assembly 26 of the stabilization element comprises a set of suction lines 60, each coupled at one end to a respective one of ports 54, and at the other end to vacuum source 92 (FIG. 1). In this configuration, each suction port acts substantially independently of each of the other ports, and is therefore unaffected by whether the other ports are in contact with the heart.

Figure 4:
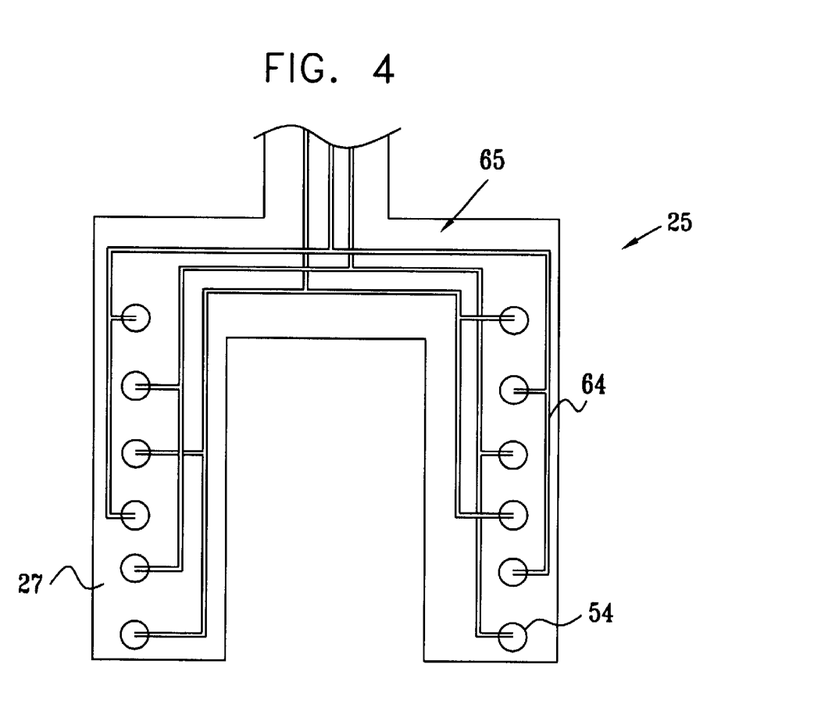

FIG. 4 is a schematic illustration of stabilization element 25, in accordance with another preferred embodiment of the present invention. By contrast to the embodiment shown in FIG. 3, in this embodiment of the present invention a suction control assembly 65 comprises one or more multi-port suction lines 64, each of which has a plurality of suction ports 54 coupled thereto. This configuration allows greater simplicity of the stabilization element, by reducing the number of suction lines used to hold the surface of the heart in contact with the stabilization element. Preferably, a sufficient number of suction lines 64 are utilized such that even if one of the ports on a multi-port suction line fails—thereby generally disabling the other ports on the same line—one or more other ports not coupled to the same line will still maintain their seals with the segment of the heart.

Figure 5:
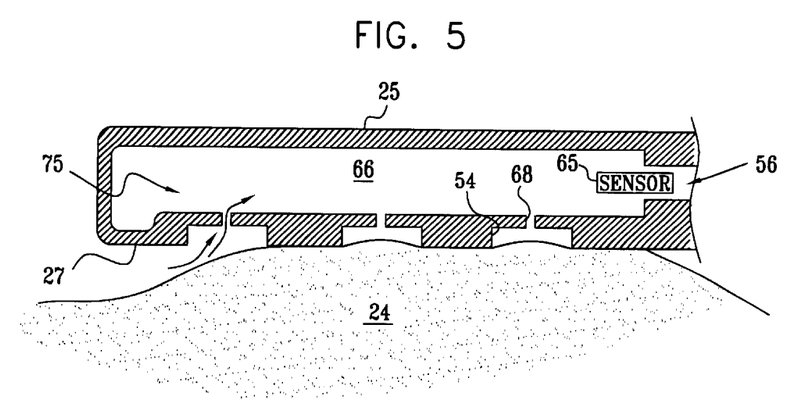

FIG. 5 is a schematic illustration of stabilization element 25, in accordance with yet another preferred embodiment of the present invention. In this embodiment, a suction control assembly 75 comprises a relatively-large chamber 66, which is coupled to convey a suction force generated by vacuum source 92 through respective small orifices 68 to a plurality of ports 54 on surface 27 of the stabilization element. Typically, but not necessarily, the chamber is disposed within the stabilization element, as shown in FIG. 5. Preferably, the volume of chamber 66 is sufficiently large, and the cross-sectional areas of orifices 68 are sufficiently small, such that if one of suction ports 54 loses its seal with the heart, and air enters the chamber through the orifice coupled to the port (as shown in FIG. 5), then the negative pressure within the chamber will not be significantly affected. Since the overall negative pressure within the chamber substantially does not change when one of the ports coupled thereto loses its seal with the heart, the other ports coupled to the chamber will continue to function.

Alternatively or additionally, a sensor 65 coupled to chamber 66 conveys to control unit 90 a signal responsive to air pressure within the chamber. When all of the suction ports are sealed to the surface of the heart, there is no flow of air within the chamber, and the pressure therein is substantially the pressure generated by vacuum source 92. However, if one of the ports loses it seal, as shown in FIG. 5, then air enters the chamber through that port, and leaves the chamber through an exit 56 coupled to lines 35. Preferably, control unit 90 actuates vacuum source 92 to increase the rate of airflow through lines 35 from chamber 66 when sensor 65 indicates a drop in the magnitude of the air pressure in the chamber. Further preferably, the vacuum source is sufficiently powerful such that the increase in airflow restores the chamber pressure to substantially the same value as prior to the port losing its seal with the heart. Still further preferably, exit 56 and lines 35 are of sufficient size and material strength to allow the passage therethrough of the increased flow of air.

Figure 6:
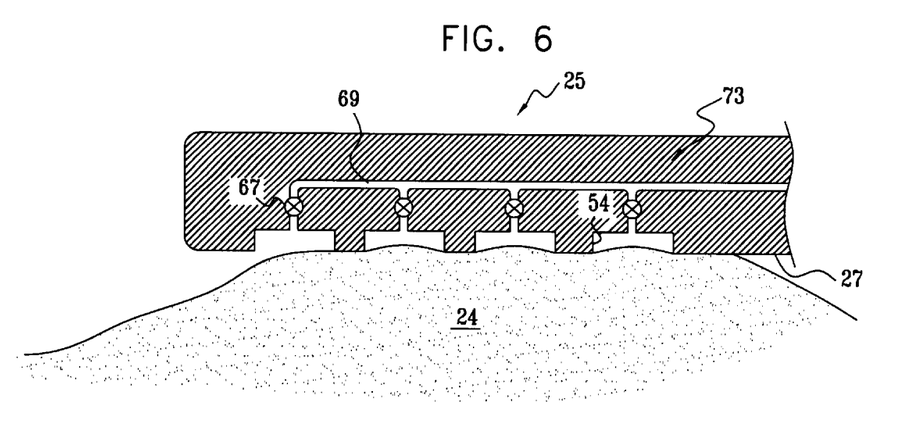

FIG. 6 is a schematic illustration of stabilization element 25, in accordance with still another preferred embodiment of the present invention. In this embodiment, a suction control assembly 73 comprises a multi-port suction line 69, which is coupled to ports 54 through respective valves 67. Each valve is adapted to close when the suction port coupled thereto loses its seal with the surface of the heart. In this manner, even when a plurality of ports are coupled to the same line, the failure of one of the ports does not adversely affect the functioning of the other ports. While valves 67 typically close automatically responsive to air-flow therethrough, for some applications, the valves are controlled by control unit 90.

Figure 7:
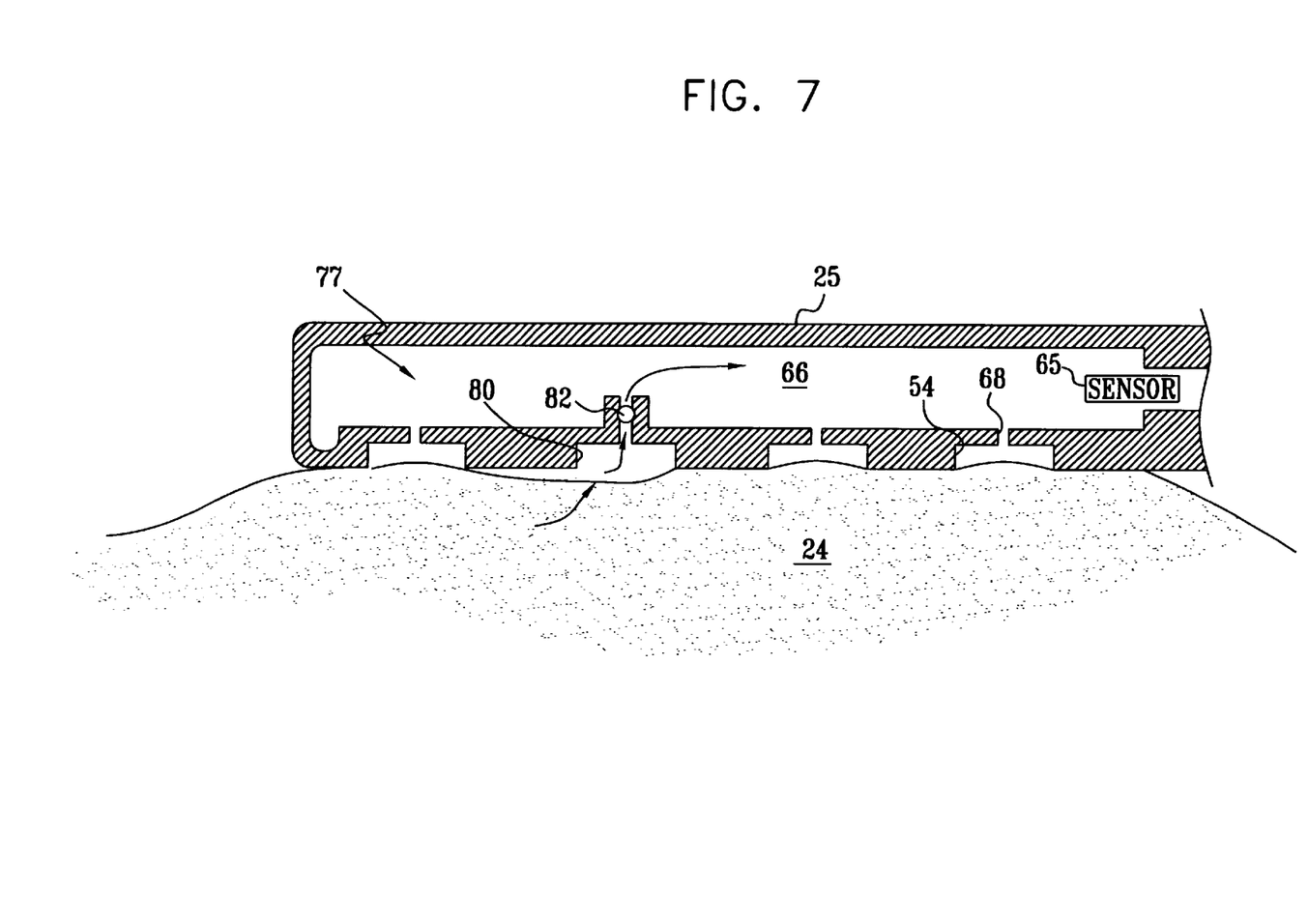

FIG. 7 is a schematic illustration of stabilization element 25, in accordance with a further preferred embodiment of the present invention. In this embodiment, a suction control assembly 77 comprises chamber 66, which is coupled to convey a suction force through respective small orifices 68 to suction ports 54, and through a pressure regulator 82 to a test port 80. Suction control assembly 77 functions in a generally similar manner to assembly 75, described hereinabove with reference to FIG. 5. However, in contrast to assembly 75, whose ports all apply substantially the same level of suction to the heart when they all form a seal therewith, regulator 82 causes test port 80 to apply to the heart a level of suction whose magnitude is lower than the suction applied to the other ports of assembly 77. Preferably, control unit 90 or the surgeon modulates the extent to which pressure regulator 82 reduces the magnitude of the pressure, such that the pressure applied by test port 80 can be changed, for example, from 10% lower to 20% lower than that of the other ports coupled to chamber 66. Alternatively, regulator 82 reduces the magnitude of the pressure by a generally fixed amount.

It will be appreciated that there are a variety of methods known in the art of pressure regulation, which may be adapted for use with this embodiment of the present invention. For example, port 80 may be shaped such that, for a given pressure in chamber 66, port 80 is more likely than the other ports to lose its seal with the heart. Preferably, an aspect of the shape of the port can be varied by the surgeon prior to or during the procedure, so as to control the extent to which the suction applied to the heart by port 80 is lower than that applied by the other ports. Alternatively or additionally, other active or passive means are employed for reducing the pressure.

In a typical operational mode, control unit 90 reduces the magnitude of the negative pressure in chamber 66 until test port 80 loses its seal with the surface of the heart. In almost all cases, port 80 separates from the heart before the other ports, because the suction which it applies to the heart is weaker than that applied by the other ports. As described hereinabove with reference to FIG. 5, when one of the ports coupled to chamber 66 loses its seal with the heart, the other ports generally maintain their seal. Advantageously, the embodiment shown in FIG. 7 allows the surgeon to: (a) reduce the pressure in chamber 66 to a level which is generally lower than would be possible with prior art mechanical stabilizers, and thereby reduce injury associated with the suction, and (b) generally assure that during a substantial portion of the procedure, the other ports will remain sealed to the heart, because they apply a higher level of suction than does the test port.

Figure 8:
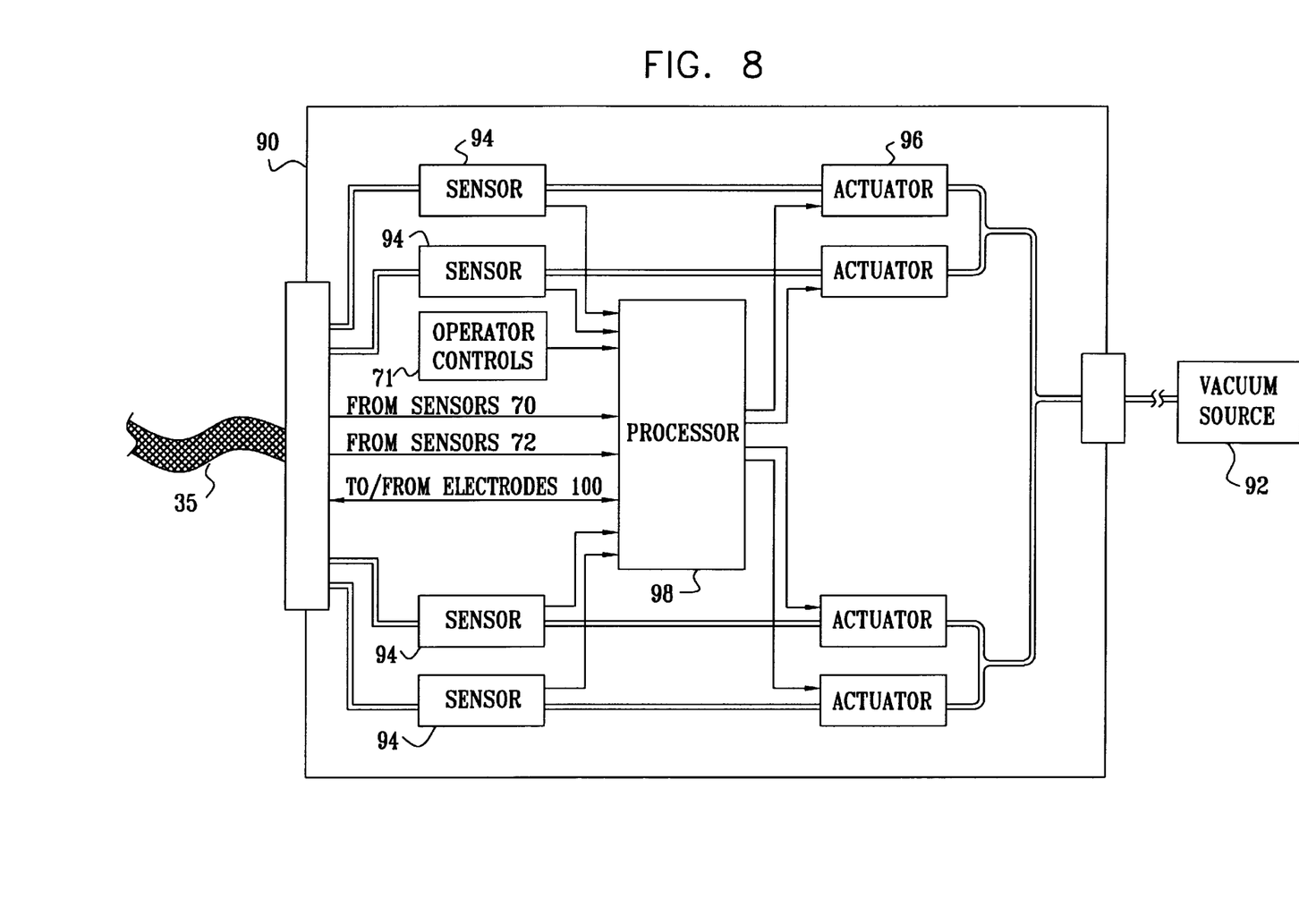
FIG. 8 is a schematic block diagram of a control unit, which conveys negative air pressure to the stabilization element, in accordance with a preferred embodiment of the present invention.

FIG. 8 is a schematic block diagram of control unit 90, which modulates aspects of the suction applied to stabilization element 25, in accordance with a preferred embodiment of the present invention. It will be appreciated by one skilled in the art that the configurations of the various elements shown in FIG. 8 and in the other figures are shown by way of illustration and not limitation. There are many other ways to arrange suction ports, valves, suction lines, sensors, etc., such that the loss of the seal of a single suction port with the heart will not substantially reduce the level of suction applied by some or all of the other ports.

Preferably, control unit 90 comprises one or more air-flow and/or air-pressure sensors 94, which are coupled to convey signals to a processor 98 of the control unit responsive to characteristics of the suction being applied to the various suction ports 54. In FIG. 8, for example, sensors 94 are coupled to individual suction lines that run through lines 35 to a plurality of ports 54, such as are shown in FIG. 3, or to clusters of ports 54, such as are shown in FIG. 4. Preferably, processor 98 analyzes the signals from sensors 94, and, responsive thereto, modulates the states of respective actuators 96, so as to achieve a desired level of suction at each of the suction ports. Alternatively or additionally, processor 98 modulates the actuators based on instructions entered through operator controls 71, and/or based on signals received from motion sensors 70, supplemental sensors 72, and/or electrodes 100. In a preferred embodiment, the actuators comprise continuously-adjustable valves. Alternatively or additionally, processor 98 directly controls the pressure output of vacuum source 92.

Typically, processor 98 comprises an integrated circuit or other electronic circuitry that is capable of evaluating a plurality of inputs and controlling hardware responsive to the evaluation. In this case, operator controls 71 preferably comprise a digital interface, such as a keypad (not shown). In other applications, however, the processor is substantially only mechanical, comprising, for example, a series of valves or other flow regulators. For these applications, the operator controls preferably comprise one or more mechanical elements, such as knobs or switches, which regulate the suction applied at one or more of suction ports 54.

In a preferred operational mode, processor 98 causes at least some of actuators 96 to reduce the level of suction applied by some or all of suction ports 54, until at least one of the ports loses its seal with the surface of the heart. At this point, most or all of the other ports preferably continue to apply suction. It is noted that this embodiment of the present invention allows stabilization element 25, configured according to any of the configurations in FIGS. 3–7, to operate at suction levels significantly lower than would be necessary if it was required to maintain a seal between every one of the suction ports and the surface of heart 20.

Optionally, processor 98 varies the level of suction applied by one or more of the ports, responsive to measurements by sensors 94 and/or measurements by sensors in or on the stabilization element, which are indicative of the number of suction ports which are effectively securing heart 20. Thus, for example, the processor may regulate actuators 96 such that, from a total of eight suction ports, between four and six suction ports will generally make a suction seal with the heart. Alternatively or additionally, processor 98 sets the level of suction at the various suction ports based on signals from supplemental sensors 72 and/or motion sensors 70, indicative of, for example, heart rate, left ventricular pressure (LVP), or motion of the heart. In a preferred operational mode, suction is decreased responsive to a decrease in the patient's heart rate, because reduced heart rate is typically associated with a lower probability that the suction ports will lose effective contact.

Alternatively or additionally, processor 98 modulates the level of suction applied through ports 54 to heart 20 in coordination with other means for stabilizing the segment of the heart, e.g., cardioplegia-inducing drugs, mechanical force applied by the stabilization element, or electrical signals applied to the heart. For example, if the application of cardioplegia-inducing drugs is being decreased, the level of suction may be increased. Alternatively, if processor 98 is driving electrodes 100 to apply motion-reduction electrical signals to the heart (as described, for example, in some or all of the patent applications which are incorporated herein by reference), then the suction applied to the heart is preferably reduced in response to the reduced demand for physical stabilization of the heart.

Although preferred embodiments are described hereinabove with reference to reducing motion of segment 24 of heart 20 in order to enable surgery on the segment, it will be understood that the present invention may be used for other purposes, such as to enhance a physician's ability to perform diagnostic tests on the segment.

Furthermore, the principles of the present invention are applicable not only to the heart, but also to controlling local motion in segments of other types of tissue, such as skeletal muscle and smooth muscle (e.g., portions of the gastrointestinal tract, the uterus, and other organs).

It will be appreciated by persons skilled in the art that the present invention is not limited to what has been particularly shown and described hereinabove. Rather, the scope of the present invention includes both combinations and subcombinations of the various features described hereinabove and in the articles, patents and patent applications incorporated herein by reference, as well as variations and modifications thereof that are not in the prior art, which would occur to persons skilled in the art upon reading the foregoing description.

What is claimed is:

1. Apparatus for performing a medical procedure on a beating heart, comprising:
   a stabilization element, adapted to be applied to a segment of the heart in order to reduce motion of the segment;
   a plurality of suction ports, positioned on the stabilization element so as to form respective seals with the segment of the heart while the stabilization element is applied to the segment, which suction ports are adapted to apply suction forces to the segment of the heart so as to maintain the segment in contact with the stabilization element; and
   a suction control assembly, coupled to the ports, such that at least one of the suction ports is adapted to maintain its seal with the segment of the heart even when another one of the suction ports does not form a seal with the segment of the heart,
   wherein the suction control assembly comprises a valve coupled to one of the suction ports, said valve being adapted to close when the suction port coupled thereto does not form a seal with the segment of the heart.

2. Apparatus for performing a medical procedure on a beating heart, comprising:
   a stabilization element, adapted to be applied to a segment of the heart in order to reduce motion of the segment;
   a plurality of suction ports, positioned on the stabilization element so as to form respective seals with the segment of the heart while the stabilization element is applied to the segment, which suction ports are adapted to apply suction forces to the segment of the heart so as to maintain the segment in contact with the stabilization element; and
   a suction control assembly, coupled to the ports, such that at least one of the suction ports is adapted to maintain its seal with the segment of the heart even when another one of the suction ports does not form a seal with the segment of the heart,
   wherein the suction control assembly comprises a chamber having negative air pressure therein when the stabilization element is applied to the segment of the heart, wherein the chamber is coupled through respective orifices to the suction ports, and wherein a characteristic of the orifices is such that, when one of the suction ports does not form a seal with the segment of the heart, a magnitude of the negative air pressure within the chamber is maintained to such an extent that one or more of the other suction ports maintain their seals with the segment of the heart, and
   wherein the characteristic of the orifices comprises cross-sectional areas of the orifices.

3. Apparatus for performing a medical procedure on a beating heart, comprising:
   a stabilization element, adapted to be applied to a segment of the heart in order to reduce motion of the segment;
   a plurality of suction ports, positioned on the stabilization element so as to form respective seals with the segment of the heart while the stabilization element is applied to the segment, which suction ports are adapted to apply suction forces to the segment of the heart so as to maintain the segment in contact with the stabilization element;
   a suction control assembly, coupled to the ports, such that at least one of the suction ports is adapted to maintain its seal with the segment of the heart even when another one of the suction ports does not form a seal with the segment of the heart;
   a vacuum source, adapted to generate negative air pressure;
   a control unit, adapted to couple the negative air pressure to the plurality of suction ports, so as to apply to the segment of the heart the suction forces which maintain the segment in contact with the stabilization element; and
   a force sensor, adapted to convey to the control unit a force signal responsive to a force applied by the stabilization element to the segment of the heart, wherein the control unit is adapted to modulate a magnitude of the negative air pressure applied to one or more of the suction ports responsive to the force signal.

4. Apparatus for performing a medical procedure on a beating heart, comprising:
   a stabilization element, adapted to be applied to a segment of the heart in order to reduce motion of the segment;
   a plurality of suction ports, positioned on the stabilization element so as to form respective seals with the segment of the heart while the stabilization element is applied to the segment, which suction ports are adapted to apply suction forces to the segment of the heart so as to maintain the segment in contact with the stabilization element;
   a suction control assembly, coupled to the ports, such that at least one of the suction ports is adapted to maintain its seal with the segment of the heart even when another one of the suction ports does not form a seal with the segment of the heart;
   a vacuum source, adapted to generate negative air pressure;
   a control unit, adapted to couple the negative air pressure to the plurality of suction ports, so as to apply to the segment of the heart the suction forces which maintain the segment in contact with the stabilization element; and
   a sensor, adapted to convey to the control unit a sensor signal indicative of a number of the suction ports not forming a seal with the segment of the heart, wherein the control unit is adapted to modulate a magnitude of the negative air pressure applied to two or more of the ports, so as to generally maintain a determined number of the suction ports not forming respective seals with the segment of the heart.

5. Apparatus according to claim 4, wherein the control unit is adapted to modulate the magnitude of the negative air pressure applied to two or more of the ports, so as to generally maintain exactly one of the suction ports not forming a seal with the segment of the heart.

6. Apparatus for performing a medical procedure on a beating heart, comprising:
   a stabilization element, adapted to be applied to a segment of the heart in order to reduce motion of the segment;
   a plurality of suction ports, positioned on the stabilization element so as to form respective seals with the segment of the heart while the stabilization element is applied to the segment, which suction ports are adapted to apply suction forces to the segment of the heart so as to maintain the segment in contact with the stabilization element;

a suction control assembly, coupled to the ports, such that at least one of the suction ports is adapted to maintain its seal with the segment of the heart even when another one of the suction ports does not form a seal with the segment of the heart;

a vacuum source, adapted to generate negative air pressure;

a control unit, adapted to couple the negative air pressure to the plurality of suction ports, so as to apply to the segment of the heart the suction forces which maintain the segment in contact with the stabilization element; and a motion sensor, adapted to convey to the control unit a motion signal responsive to motion of the heart, wherein the control unit is adapted to modulate a magnitude of the negative air pressure applied to one or more of the suction ports responsive to the motion signal.

7. Apparatus according to claim 6, wherein the motion sensor is fixed to the stabilization element.

8. Apparatus according to claim 6, wherein the control unit is adapted to reduce the magnitude of the negative air pressure responsive to a motion signal indicative of reduced motion of the heart.

9. Apparatus according to claim 6, wherein the control unit is adapted to increase the magnitude of the negative air pressure responsive to a motion signal indicative of increased motion of the heart.

10. Apparatus for performing a medical procedure on a beating heart, comprising:

a stabilization element, adapted to be applied to a segment of the heart in order to reduce motion of the segment;

a plurality of suction ports, positioned on the stabilization element so as to form respective seals with the segment of the heart while the stabilization element is applied to the segment, which suction ports are adapted to apply suction forces to the segment of the heart so as to maintain the segment in contact with the stabilization element;

a suction control assembly, coupled to the ports, such that at least one of the suction ports is adapted to maintain its seal with the segment of the heart even when another one of the suction ports does not form a seal with the segment of the heart;

a vacuum source, adapted to generate negative air pressure;

a control unit, adapted to couple the negative air pressure to the plurality of suction ports, so as to apply to the segment of the heart the suction forces which maintain the segment in contact with the stabilization element; and a sensor, coupled to the control unit and to the suction ports, wherein the control unit is adapted to reduce a magnitude of the negative air pressure applied to two or more of the ports, and to terminate reducing the magnitude of the negative air pressure when the sensor conveys a sensor signal indicative of one or more of the suction ports not forming respective seals with the segment of the heart.

11. Apparatus according to claim 10, wherein the sensor comprises an air-pressure sensor.

12. Apparatus according to claim 10, wherein the sensor comprises an air-flow sensor.

13. Apparatus for performing a medical procedure on a beating heart, comprising:

a stabilization element, adapted to be applied to a segment of the heart in order to reduce motion of the segment;

a plurality of suction ports, positioned on the stabilization element so as to form respective seals with the segment of the heart while the stabilization element is applied to the segment, which suction ports are adapted to apply suction forces to the segment of the heart so as to maintain the segment in contact with the stabilization element; and a suction control assembly, coupled to the ports, such that at least one of the suction ports is adapted to maintain its seal with the segment of the heart even when another one of the suction ports does not form a seal with the segment of the heart, wherein the plurality of suction ports comprise:
a test port; and
a set of other ports,
wherein, for a given level of negative air pressure applied to the test port and to the set of other ports, the other ports are adapted to have a higher probability than the test port of remaining sealed to the segment of the heart.

14. Apparatus according to claim 13, wherein the test port comprises a pressure regulator including an input and an output thereof, the pressure regulator being adapted to be coupled at the input to air at a first magnitude of air pressure, and to be coupled to apply, at the output, air at a second magnitude of air pressure which is lower than the first magnitude.

15. A method for performing a medical procedure on a beating heart, comprising:

applying a stabilization element to a segment of the heart, so as to reduce motion of the segment; and applying suction forces to the segment of the heart through a plurality of suction ports that are positioned on the stabilization element, so as to form respective seals with the segment of the heart while the stabilization element is applied to the segment, and so as to maintain the segment in contact with the stabilization element, such that at least one of the suction ports maintains its seal with the segment of the heart even when another one of the suction ports does not form a seal with the segment of the heart, wherein applying the stabilization element to the segment of the heart comprises applying the element so as to enable a diagnostic medical procedure to be performed on the heart.

16. A method for performing a medical procedure on a beating heart, comprising:

applying a stabilization element to a segment of the heart, so as to reduce motion of the segment; and applying suction forces to the segment of the heart through a plurality of suction ports that are positioned on the stabilization element, so as to form respective seals with the segment of the heart while the stabilization element is applied to the segment, and so as to maintain the segment in contact with the stabilization element, such that at least one of the suction ports maintains its seal with the segment of the heart even when another one of the suction ports does not form a seal with the segment of the heart, wherein applying the suction forces comprises closing a valve coupled to one of the suction ports when the suction port coupled to the valve does not form a seal with the segment of the heart.

17. A method for performing a medical procedure on a beating heart, comprising:

applying a stabilization element to a segment of the heart, so as to reduce motion of the segment; and applying suction forces to the segment of the heart through a plurality of suction ports that are positioned on the stabilization element, so as to form respective seals with the segment of the heart while the stabilization element is applied to the segment, and so as to maintain the segment in contact with the stabilization element, such that at least one of the suction ports maintains its seal with the segment of the heart even when another one of the suction ports does not form a seal with the segment of the heart, wherein applying the suction forces comprises regulating negative air pressure applied to the suction ports such that a first one of the suction ports applies to the segment of the heart a first magnitude of negative air pressure, and a second one of the suction ports applies to the segment of the heart a second magnitude of negative air pressure, different from the first magnitude of negative air pressure, and wherein regulating comprises:

reducing the first and second magnitudes of negative air pressure, while generally simultaneously regulating the second magnitude of negative air pressure to be lower than the first magnitude; and discontinuing reducing the magnitudes of negative air pressure when the first port forms a seal and the second port does not form a seal.

18. A method for performing a medical procedure on a beating heart, comprising:

applying a stabilization element to a segment of the heart, so as to reduce motion of the segment; and applying suction forces to the segment of the heart through a plurality of suction ports that are positioned on the stabilization element, so as to form respective seals with the segment of the heart while the stabilization element is applied to the segment, and so as to maintain the segment in contact with the stabilization element, such that at least one of the suction ports maintains its seal with the segment of the heart even when another one of the suction ports does not form a seal with the segment of the heart, and comprising receiving a force signal responsive to a force applied by the stabilization element to the segment of the heart, wherein applying the suction forces comprises modulating a magnitude of negative air pressure applied to one or more of the suction ports responsive to the force signal.

19. A method for performing a medical procedure on a beating heart, comprising:

applying a stabilization element to a segment of the heart, so as to reduce motion of the segment; and applying suction forces to the segment of the heart through a plurality of suction ports that are positioned on the stabilization element, so as to form respective seals with the segment of the heart while the stabilization element is applied to the segment, and so as to maintain the segment in contact with the stabilization element, such that at least one of the suction ports maintains its seal with the segment of the heart even when another one of the suction ports does not form a seal with the segment of the heart, wherein applying the suction forces comprises:

reducing a magnitude of the negative air pressure applied to two or more of the ports;

receiving a signal which is indicative of one or more of the suction ports losing their respective seals with the segment of the heart responsive to the reduced magnitude of the negative air pressure; and terminating reducing the magnitude of the negative air pressure responsive to receiving the signal.

20. A method for performing a medical procedure on a beating heart, comprising:

applying a stabilization element to a segment of the heart, so as to reduce motion of the segment; and applying suction forces to the segment of the heart through a plurality of suction ports that are positioned on the stabilization element, so as to form respective seals with the segment of the heart while the stabilization element is applied to the segment, and so as to maintain the segment in contact with the stabilization element, such that at least one of the suction ports maintains its seal with the segment of the heart even when another one of the suction ports does not form a seal with the segment of the heart, and comprising receiving a motion signal responsive to motion of the heart, wherein applying the suction forces comprises modulating a magnitude of the negative air pressure applied to one or more of the suction ports responsive to the motion signal.

21. A method according to claim 20, wherein modulating the magnitude of the negative air pressure comprises reducing the magnitude of the negative air pressure responsive to a motion signal indicative of reduced motion of the heart.

22. A method according to claim 20, wherein modulating the magnitude of the negative air pressure comprises increasing the magnitude of the negative air pressure responsive to a motion signal indicative of increased motion of the heart.

23. A method for performing a medical procedure on a beating heart, comprising:

applying a stabilization element to a segment of the heart, so as to reduce motion of the segment; and applying suction forces to the segment of the heart through a plurality of suction ports that are positioned on the stabilization element, so as to form respective seals with the segment of the heart while the stabilization element is applied to the segment, and so as to maintain the segment in contact with the stabilization element, such that at least one of the suction ports maintains its seal with the segment of the heart even when another one of the suction ports does not form a seal with the segment of the heart, and comprising driving an electrode to apply a signal to the heart which further reduces motion of the heart.

24. A method according to claim 23, wherein applying the suction forces comprises regulating a magnitude of the suction forces applied by one or more of the suction ports to the segment of the heart in conjunction with driving the electrode to apply the signal.

25. A method for performing a medical procedure on a beating heart, comprising:

applying a stabilization element to a segment of the heart, so as to reduce motion of the segment; and applying suction forces to the segment of the heart through a plurality of suction ports that are positioned on the stabilization element, so as to form respective seals with the segment of the heart while the stabilization element is applied to the segment, and so as to maintain the segment in contact with the stabilization element, such that at least one of the suction ports maintains its seal with the segment of the heart even when another one of the suction ports does not form a seal with the segment of the heart, and comprising receiving a sensor signal indicative of a number of the suction ports not forming a seal with the segment of the heart, wherein applying the suction forces comprises modulating a magnitude of the negative air pressure applied to two or more of the ports, so as to generally maintain a determined number of the suction ports not forming respective seals with the segment of the heart.

26. A method according to claim 25, wherein modulating the magnitude of the negative air pressure comprises modulating the pressure so as to generally maintain exactly one of the suction ports not forming a seal with the segment of the heart.

* * * * *